(12) United States Patent
Aboussekhra et al.

(10) Patent No.: US 10,100,275 B2
(45) Date of Patent: Oct. 16, 2018

(54) METHOD FOR GENERATING HUMAN MULTIPOTENT MAMMARY STEM CELLS FROM NORMAL PRIMARY BREAST LUMINAL CELLS

(71) Applicant: KING FAISAL SPECIALIST HOSPITAL & RESEARCH CENTRE, Riyadh (SA)

(72) Inventors: Abdelilah Aboussekhra, Riyadh (SA); Huda H. Al-Khlaf, Riyadh (SA); Hazem Ghebeh, Riyadh (SA)

(73) Assignee: KING FAISAL SPECIALIST HOSPITAL & RESEARCH CENTRE, Riyadh (SA)

( * ) Notice: Subject to any disclaimer, the term of this patent is extended or adjusted under 35 U.S.C. 154(b) by 0 days.

(21) Appl. No.: 15/461,043

(22) Filed: Mar. 16, 2017

(65) Prior Publication Data

US 2018/0265841 A1    Sep. 20, 2018

(51) Int. Cl.
*A61K 35/12* (2015.01)
*C12N 5/071* (2010.01)
*C12N 5/0775* (2010.01)

(52) U.S. Cl.
CPC ............ *C12N 5/0602* (2013.01); *A61K 35/12* (2013.01); *C12N 2501/2308* (2013.01)

(58) Field of Classification Search
CPC .. C12N 5/0662; C12N 5/0063; C12N 5/0664; C12N 5/0665; C12N 5/0666; C12N 5/0668; C12N 5/0631; C12N 2501/2308; C12N 5/071; C12N 5/074; A61K 35/12
USPC ....................................................... 435/371
See application file for complete search history.

(56) References Cited

U.S. PATENT DOCUMENTS

2014/0120542 A1* 5/2014 Tlsty .................... C12N 5/0607
                                                                              435/6.12

OTHER PUBLICATIONS

Yu et al. Isolation of a Novel Population of Multipotent Adult Stem Cells From Human Hair Follicles; American Journal of Pathology, vol. 168, No. 6 pp. 1879-1888. (Year: 2006).*

Wilkerson, G. K. Development and Utilization of a Macaque-Based Mammosphere Culture Technique for Breast Cancer Research; Colorado State University, Proquest Dissertations Publishing, Proquest Numer 10191793, pp. 1-178. (Year: 2016).*
Ethier et al. Differential Isolation of Normal Luminal Mammary Epithelial Cells and Breast Cancer Cells From Primary and Metastatic Sites Using Selective Media; Cancer Research, vol. 53, pp. 627-635. (Year: 1993).*
"Breast Cancer Statistics." *World Cancer Research Fund International*, Accessed: May 15, 2017, http://www.wcrf.org/int/cancer-facts-figures/data-specific-cancers/breast-cancer-statistics.
Deng, G. et al., "Loss of Heterozygosity in Normal Tissue Adjacent to Breast Carcinomas." *Science*, Dec. 1996, 274:2057-2059, doi: 0.1126/science.274.5295.2057.
Ercan, C. et al., "Mammary Development and Breast Cancer: The Role of Stem Cells." *Curr. Mol. Med.*, Jun. 2011, 11(4):270-285, doi: 10.2174/156652411795678007.
Kordon, E.G., Smith G.H., "An Entire Functional Mammary Gland May Comprise the Progeny from a Single Cell." *Development*, Apr. 1998, 125:1921-1930.
Lakhani, S.R. et al., "Detection of Allelic Imbalance Indicates that a Proportion of Mammary Hyperplasia of Usual Type are Clonal, Neoplastic Proliferations." *Lab Invest.*, Jan. 1996, 74(1):Abstract.
Shackleton, M. et al., "Generation of a Functional Mammary Gland from a Single Stem Cell." *Nature*, Jan. 2006, 439:84-88, doi: 10.1038/nature04372.
Wang, R.-H., "The New Portrait of Mammary Gland Stem Cells." *Int. J. Biol. Sci.*, Jun. 2006, 2(4):186-187, doi: 10.7150/ijbs.2.186.

* cited by examiner

*Primary Examiner* — Scott Long
*Assistant Examiner* — Paul C Martin
(74) *Attorney, Agent, or Firm* — Saliwanchik, Lloyd & Eisenschenk

(57) ABSTRACT

The invention relates to methods for generating multipotent mammary stem cells from isolated and cultured human breast luminal cells. The method comprises the steps: 1. isolating and growing normal differentiated cells in vitro; 2. treating the differentiated cells with either a conditioned medium from active fibroblasts or cytokine. The invention also relates to multipotent mammary stem cells, cultures of the multipotent stem cells, differentiated cells, tissues, organs derived from the culture multipotent stem cells isolated by the methods disclosed and therapeutic and other uses for those cells thereof.

14 Claims, 5 Drawing Sheets
Specification includes a Sequence Listing.

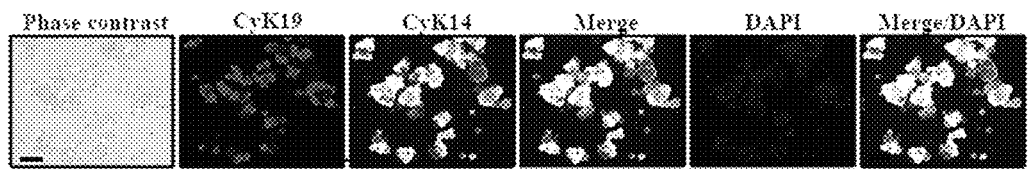
FIG. 3B
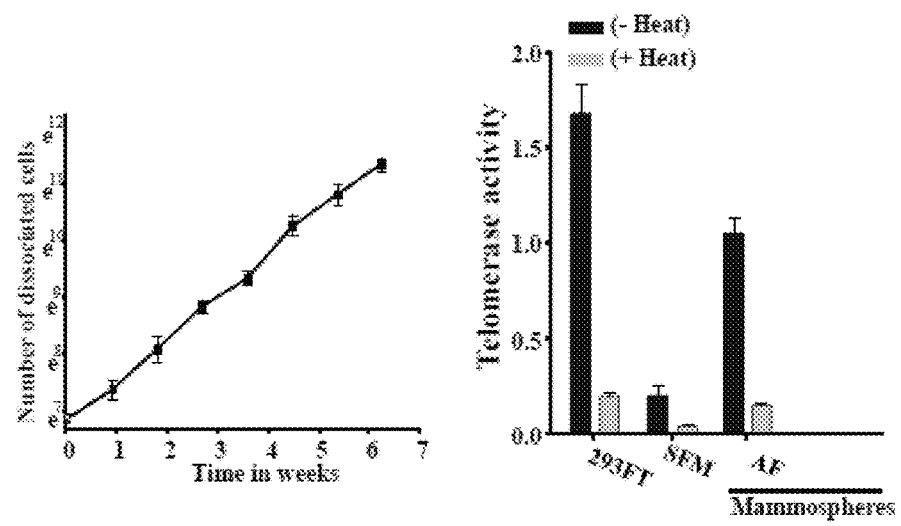
FIG. 4A
FIG. 4B
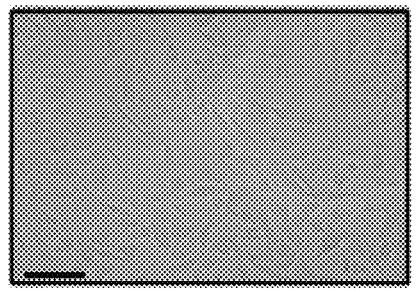
FIG. 5A

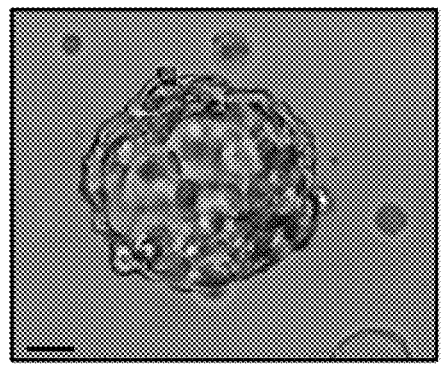
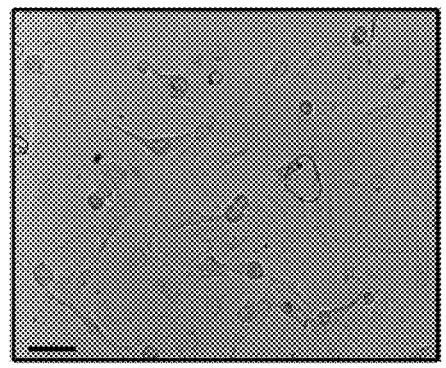
FIG. 6A          FIG. 6B
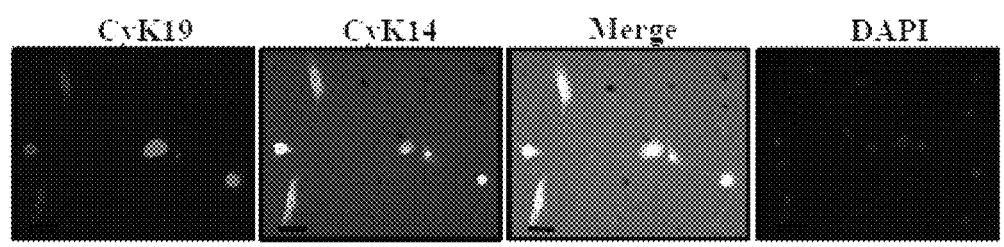
FIG. 6C
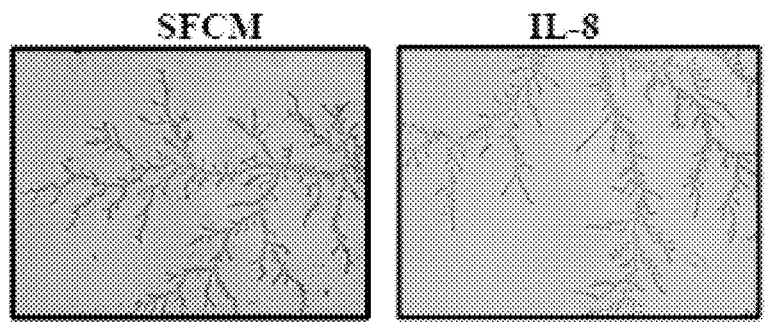
FIG. 7A          FIG. 7B

SEQUENCE LISTING

```
<160> NUMBER OF SEQ ID NOS: 1

<210> SEQ ID NO 1
<211> LENGTH: 99
<212> TYPE: PRT
<213> ORGANISM: Homo sapiens
<220> FEATURE:
<221> NAME/KEY: MISC_FEATURE
<222> LOCATION: (1)..(99)
<223> OTHER INFORMATION: human interleukin-8

<400> SEQUENCE: 1

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
```

```
                    20                  25                  30

Arg Cys Gln Cys Ile Lys Thr Tyr Ser Lys Pro Phe His Pro Lys Phe
                35                  40                  45

Ile Lys Glu Leu Arg Val Ile Glu Ser Gly Pro His Cys Ala Asn Thr
            50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser
```

METHOD FOR GENERATING HUMAN MULTIPOTENT MAMMARY STEM CELLS FROM NORMAL PRIMARY BREAST LUMINAL CELLS

The Sequence Listing for this application is labeled "SeqList-16Mar17-ST25.txt", which was created on Mar. 16, 2017, and is 2 KB. The entire content is incorporated herein by reference in its entirety.

TECHNICAL FIELD

The invention relates to methods for generating multipotent mammary stem cells from isolated and cultured human breast luminal cells. The invention also relates to appropriate culture media used by the methods disclosed; multipotent mammary stem cells, cultures of the multipotent stem cells, differentiated cells derived from the culture multipotent stem cells isolated by the methods disclosed and therapeutic uses for those cells.

BACKGROUND OF THE INVENTION

Mammary stem cells are multipotent adult stem cells that reside in the mammary gland, have self-renewal properties by dividing and differentiating into the specialized mammary epithelial cells. Mammary stem cells contribute to the development of the mammary gland during puberty and are responsible for the significant expansion during pregnancy. Mammary stem cells give rise to mature epithelium of the mammary gland which is composed of two cellular lineages: The luminal lineage and the myoepithelial lineage via a series of lineage-restricted intermediates.

In human breast tissue, the observation of identical chromosomal alterations in contiguous regions of human breast epithelium has implied the presence of mammary stem cells (Deng et al., Loss of heterozygosity in normal tissue adjacent to breast carcinomas. Science 1996, 274:2057-2059; Lakhani et al., Detection of allelic imbalance indicates that a proportion of mammary hyperplasia of usual type are clonal, neoplastic proliferations. Lab Invest 1996, 74:129-135.). In the recent ten years, much progress has been made in the identification of signaling pathways that function in mammary stem cells to control self-renewal, lineage commitment and epithelial differentiation in the normal mammary gland. Meanwhile, the same signaling pathways that control physiological mammary development and homeostasis are also often found deregulated in breast cancer (Ercan, et al., Mammary Development and Breast Cancer: The Role of Stem Cells, Curr Mol Med. 2011 June; 11(4): 270-285).

In recent studies, breast cancer was found to be the most common cancer in women worldwide, with nearly 1.7 million new cases diagnosed in 2012 (Internet, World Cancer Research Fund International, http://www.wcrf.org/int/cancer-facts-figures, accessed on Jun. 9, 2016). Even though treatment for breast cancer has been significantly improved and the survival rate has been increased, this disease is still a big health problem for human being. Therefore, the research concerning the mammary gland stem cell and breast cancer stem cell might provide motivations to find the complete treatment of this deadly disease (Kordon E C, Smith G H, an entire functional mammary gland may comprise the progeny from a single cell. Development. 1998; 125:1921-30). Researchers believe that once the stem cell is isolated, the signaling pathways that regulate its proliferation, self-renewal, survival and differentiation will be illustrated, and this might shed light on the mechanisms of breast cancer formation, therefore leading to a better therapeutic treatment (Wang R H, the new portrait of mammary gland stem cells. Int J Biol Sci 2006; 2(4):186-187).

In addition, the research on mammary stem cell may provide an active solution for organ transplantation. With respect to allotransplantation, the common problem is that there is no enough organ donations. With respect to xenotransplantation, it also raises many novel medical issues. For example, xenotransplantation does not overcome the problem of tissue incompatibility and furthermore, there is evidence that damaging viruses cross species barriers.

Recent success at transplanting through stem cells have provided new clinical tools to reconstitute and/or supplement bone marrow after myeloablation due to disease or damages seduced by the harmful environment. It was also reported that a single mammary stem cell can reconstitute a complete mammary gland in vivo (Shackleton M., et al., Nature. 2006 Jan. 5; 439(7072):84-8). The application of stem cells in tissue engineering, gene therapy delivery and cell therapeutics is also advancing rapidly.

However, a basic problem existed prior to the present invention. It is difficult to obtain sufficient quantities and populations of human stem cells which are capable of differentiating into most cell types. The isolation of normally occurring populations of stem cells in adult tissues is known to be technically complicated and costly due to the limited quantity found in human tissue. The harvest of these stem cells from embryos or fetal tissue is morally questionable, if not forbidden anyway for religious, legal and ethical reasons.

There is therefore a need for developing methods for generating multipotent mammary stem cells.

There is also a need to provide multipotent mammary stem cells, cultures of the multipotent stem cells, differentiated cells, tissues and also organs derived from the cultured multipotent stem cells, for their applicability in tissue engineering and cell therapeutics. This will also help scientists and researchers to gain a better understanding of mammary stem cells, and will ultimately lead to better therapies including breast cancer therapies.

There is also a further need for a source of cells that are transplantable to in vivo tissues/organs in order to replace diseased or damaged tissues/organs.

SUMMARY OF THE INVENTION

In one aspect the present invention relates to a method for generating multipotent mammary stem cells comprising the steps:

a) isolating and growing primary breast luminal cells in-vitro;

b) treating the primary breast luminal cells with either a conditioned medium from active breast stromal fibroblasts or with interleukin-8 (IL-8) in serum-free medium;

c) continuing the growth of cells until the formation of cellular aggregates, wherein preferably such growth is done in a breast luminal-cell-specific medium; and d) transferring the cells to a stem cell growth medium and growing them further until the formation of mammospheres.

BRIEF DESCRIPTION OF THE DRAWINGS

FIGS. 3A-3B are graphs of immunofluorescence test on the mammospheres obtained by the treatment with SFCM from active fibroblasts (A) OR IL-8. FIG. 3A shows that the spheres were positive for the mammosphere-specific markers cytokeratines (CyK) 5/6, 18 and 14 as well as c-Kit and Elf-5. DAPI, FITC and TRITC were used as dyes (DAPI=4', 6-Diamidino-2-phenylindole; FITC=fluorescein isothiocyanate, TRITC=tetramethyl rhodamine). Similarly, FIG. 3B presents the results obtained for cells treated with IL-8 for the mammosphere-specific markers cytokeratines 14, and 19. as well as Merge, DAPI and Merge/DAPI. "Merge" is the overlay between the 2 antibodies, and "Merge/DAPI" is the overlay between Merge and DAPI.

FIG. 4A-4B are graphs showing that the multipotent stem cells obtained by the method of the present invention exhibit high and exponential proliferative capacity as well as a high telomerase activity which is also an indicator of stemness. FIG. 4A shows the proliferation rate, and FIG. 4B shows the telomerase activity.

FIG. 5A-5C illustrates the differentiation capacity of the SFCM generated multipotent stem cells obtained by the method of the present invention. FIG. 5A shows the presence of cells with luminal and myoepithelial morphology. FIG. 5B illustrates a stain test for luminal and myoepithelial morphology for the cells produced according the method of the present invention. As shown by FIG. 5B, these cells were stained positive for the myoepithelial marker (CyK14), or the luminal marker (CyK19) or both, with lower proportion of cells that were positive for both. This indicates the ability of these mammary stem cells in the mammospheres to be differentiated into luminal and myoepithelial cells, in addition to some bipotent cells. FIG. 5C is a graph of a flow cytometry analysis showing two different populations, one corresponding to myoepithelial cells and the other one corresponding to a luminal type of cells.

FIGS. 6A-6C illustrates the differentiation capacity of the IL-8-generated mammospheres. (A) IL-8 induced mammosphere structure under microscope (6B) microscopic view of differentiated mammospheres on gelatin. (6C) Immunostaining using anti-cytokeratin-14 (CyK14) and anti-cytokeratin-19 (CyK10).

FIGS. 7A-7B shows that both IL-8- and SFCM-induced mammospheres were able to differentiate into branches on gelatin in the presence of matrigel and prolactin, which are typical structures of the branching ducts that compose the mammary gland.

DETAILED DESCRIPTION

Figures 1A, 1B:
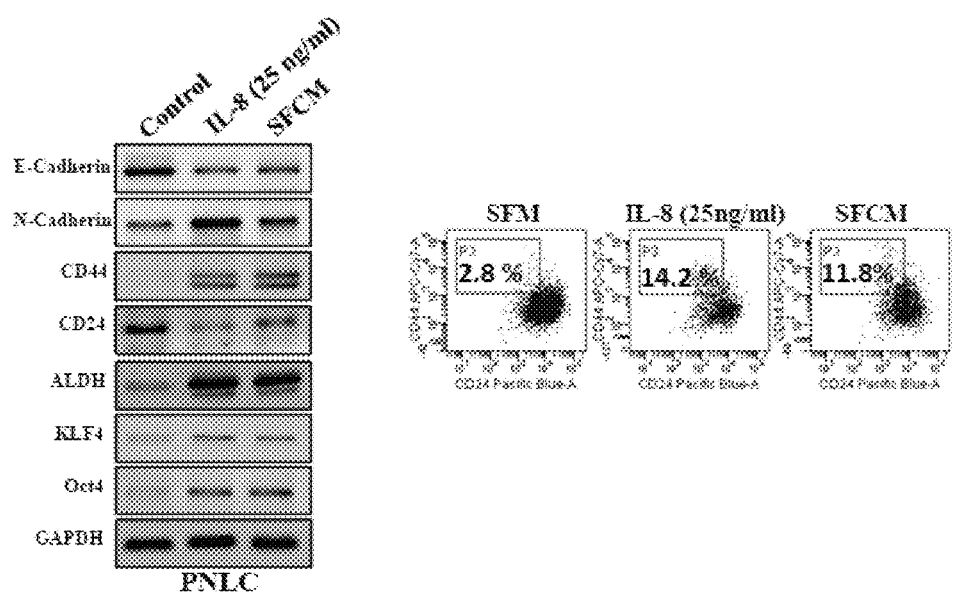
FIGS. 1A-1B are photographs of an immunoblotting analysis and flow cytometry. Serum-free conditioned medium (SFCM) from active fibroblasts or the recombinant IL-8 protein (25 ng/ml) were added onto breast primary normal luminal cells (PNLC) for 24 hours.

In one embodiment, the conditioned medium from active breast stromal fibroblasts of step b) comprises a 1:1 mixture (vol/vol) of M199 medium and F12 medium, supplemented with 0%-1% (vol/vol) serum, preferably ≤0.2% (vol/vol) serum, preferably fetal bovine serum (FBS), preferably 0.2% (vol/vol) FBS, and 0.1%-2% (vol/vol) of an antibiotic-antimycotic solution, said antibiotic-antimycotic solution comprising 10,000 units/ml penicillin, 10000 μg/ml streptomycin and 25 μg/ml amphotericin B, preferably 1% of said antibiotic-antimycotic solution, and wherein the serum-free medium of step b) comprises a 1:1 mixture (vol/vol) of M199 medium and F12 medium, said mixture being supplemented with 0%-1% (vol/vol) serum, preferably ≤0.2% (vol/vol) serum, preferably fetal bovine serum (FBS), preferably 0.2% (vol/vol) FBS, 0.1%-2% of an antibiotic-antimycotic solution, said antibiotic-antimycotic solution comprising 10,000 units/ml penicillin, 10000 μg/ml streptomycin and 25 μg/ml amphotericin B, preferably 1% (vol/vol) of said antibiotic-antimycotic solution.

As used herein, the "conditioned medium from active breast stromal fibroblasts" used in step b) is herein also sometimes referred to as a "serum-free conditioned medium from active breast stromal fibroblasts" (SFCM) or medium from active fibroblasts (AF). The term "serum-free", as used herein, is meant to refer to a medium that contains substantially no serum or, at a maximum, 0%-1% (vol/vol) serum, preferably 0.2% (vol/vol) serum, preferably at a maximum 0.2% fetal bovine serum (FBS). The term "serum-free", is used herein in the context of a "conditioned medium from active breast stromal fibroblasts" or in the context of a medium containing interleukine-8 (both media being the respective treatment media of step b) of the present invention). With respect to the serum-free conditioned medium from active breast stromal fibroblasts, this is obtained by culturing active breast stromal fibroblasts in a serum-free medium (as defined further above) for a defined period of time, e.g. 6 hours-48 hours, or 10 hours-36 hours, or 12 hours-24 hours, and thereafter separating the medium from the active breast stromal fibroblasts. The medium thus obtained is a "conditioned medium from active breast stromal fibroblasts" and is herein also sometimes referred to as a "serum-free conditioned medium from active breast stromal fibroblasts" or "SFCM" or medium from active fibroblasts (AF). It is "serum-free" in the sense that it had originally been supplemented with only 0%-1% (vol/vol) serum, preferably 0.2% (vol/vol), or less, serum, preferably with only about 0.2% fetal bovine serum (FBS). The other medium that can be used in step b) according to the present invention is a "serum-free medium" containing interleukine-8. Such serum-free medium has not undergone the "conditioning step" and is "serum-free" in the sense that it has only been supplemented, at a maximum, with 0%-1% (vol/vol) serum, preferably 0.2% (vol/vol), or less, serum, preferably with about 0.2% (vol/vol) or less fetal bovine serum. The term " . . . being supplemented with x % serum" is meant to refer to a scenario wherein the mixture or medium is supplemented with a maximum of x % serum. In one embodiment, such term may also mean that the medium or mixture has not been actively and deliberately supplemented with any serum at all and therefore contains substantially no serum.

In one embodiment, the phrase "the . . . medium comprises a . . . mixture, supplemented with . . . " is meant to be understood that the medium is a . . . mixture supplemented with . . . ".

In one embodiment, the method for generating multipotent mammary stem cells is an in-vitro method.

In one embodiment, in step c) growth of the cells is performed in a breast luminal cell-specific medium, wherein said breast luminal cell-specific medium comprises a 1:1 mixture (vol/vol) of DMEM medium and F12 medium supplemented with 1%-20% (vol/vol) fetal bovine serum (FBS), preferably 2% (vol/vol) FBS, and supplemented with 0.1%-2% (vol/vol) of an antibiotic-antimycotic solution, said antibiotic-antimycotic solution comprising 10,000 units/ml penicillin, 10000 μg/ml streptomycin and 25 μg/ml amphotericin B, preferably 1% (vol/vol) of said antibiotic-antimycotic solution, and bovine pituitary extract (5 μg/ml).

In one embodiment, said stem cell growth medium in step d) comprises MEBM medium, supplemented with 0.1%-2% (vol/vol) of an antibiotic-antimycotic solution, said antibiotic-antimycotic solution comprising 10,000 units/ml penicillin, 10000 µg/ml streptomycin and 25 µg/ml amphotericin B, preferably 1% (vol/vol) of said antibiotic-antimycotic solution, preferably 2% (vol/vol), epidermal growth factor (EGF) at 20 ng/ml, Hydrocortisone at 500 ng/ml, and recombinant human insulin-like growth factor-1 at 1-10 µg/ml, preferably 5 µg/ml.

In one embodiment, any of the above media may also additionally contain commercially available supplement solutions, such as HuMEC Supplement® available from Invitrogen or Gibco under cat. No. 12754-016. They may also contain bovine pituitary extract, preferably at a concentration of 1-20 µg/ml, more preferably at 5-10 µg/ml. In one embodiment, any of the above media may also contain further supplements or supplement cocktails, such as compositions containing antioxidants or antioxidant mixtures, insulin and/or vitamin A. An example of such supplement is B27® supplement which is commercially available from Thermofisher Scientific under cat. No. 17504-044. This may be used in any suitable concentration, such as B27®-supplement at 0.1%-10% (vol/vol), In one embodiment, treating in step b) is done for a period in the range of from 12 hours to 120 hours, preferably in the range of from 12 hours to 72 hours, more preferably in the range of from 12 hours to 48 hours, even more preferably in the range of from 12 hours to 36 hours, even more preferably in the range of from 12 hours to 30 hours, even more preferably in the range of from 20 hours to 28 hours.

In one embodiment, the primary breast luminal cells are primary human breast luminal cells, and the multipotent mammary stem cells are multipotent human mammary stem cells.

In one embodiment, said interleukin-8 is recombinant interleukin-8.

In one embodiment, said interleukin-8 is human interleukin-8, preferably having an amino acid sequence represented by MTSKLAVALLAAFLISAALCEGAVLPRSAKELRC-QCIKTYSKPFHPKFIKELRVIES GPHCANTEIIVKLS-DGRELCLDPKENWVQRVVEKFLKRAENS (SEQ ID NO: 1).

In one embodiment, said interleukin-8 is used in step b) at a concentration in the range of from 25 ng/ml to 100 ng/ml, preferably 100 ng/ml.

In one embodiment, said primary breast luminal cells are identified and isolated based on their expressing at least one or a combination of the following markers selected from Cytokeratin 18, Cytokeratin 19 and epithelial cell adhesion molecule (EpCam), wherein they are selected and isolated if they express such marker(s), and are not selected and isolated if they do not, and/or wherein said primary breast luminal cells are identified and isolated based on their nor expressing at least one or a combination of the following markers selected from Cytokeratine 14 and integrin α-6 (CD49f), wherein they are selected and isolated if they do not express such marker(s), and are not selected and not isolated if they do, and wherein, preferably, isolation occurs by enzymatic digestion using one or several proteolytic and/or collagenolytic enzyme(s) and subsequent centrifugation.

In one embodiment, the growing of said cells in step d) occurs in an environment that favors suspension cell culture, e.g. plates or dishes with a low attachment substrate.

In one embodiment, the formed mammospheres have a size in the range of from 50 µm to 200 µm.

In one embodiment, the multipotent mammary stem cells are produced by the performance of steps a)-d) and are characterized by an up-regulation of one or several or all of CD44, ALDH1, ALDH2, OCT4, KLF4 and N-cadherin, and the simultaneous expression of one or several or all myoepithelial and luminal markers selected from CyK5, CyK6, CyK14, CyK18, CyK19, c-Kit, Elf-5, in comparison to cells of the same type, i.e. primary breast luminal cells, not having undergone a treatment of steps a)-d), and are further characterized by a lower expression of CD24 and E-cadherin in comparison to primary breast luminal cells not having undergone a treatment of steps a)-d).

The passage "the multipotent mammary stem cells are . . . further characterized by a lower expression of CD24 and E-cadherin in comparison to primary breast luminal cells not having undergone a treatment of steps a)-d)", as used herein is meant to refer to multipotent mammary stem cells in accordance with the present invention in which the expression of CD24 and E-cadherin is lower than in untreated primary breast luminal cells.

In one embodiment, the method according to the present invention, further comprises the step of isolating said mammary stem cells according to the present invention.

In a further aspect, the present invention relates to a multipotent mammary stem cell or a culture of multipotent mammary stem cells generated by the method according to the present invention as defined above, said stem cell(s) being capable of differentiating into luminal cells and myoepithelial cells and being characterized by an up-regulation of one or several or all of CD44, ALDH1, ALDH2, OCT4, KLF4 and N-cadherin, and the simultaneous expression of one or several or all myoepithelial and luminal markers selected from CyK5, CyK6, CyK14, CyK18, CyK19, c-Kit, Elf-5, in comparison to cells of the same type, i.e. primary breast luminal cells, not having undergone a treatment of steps a)-d), and are further characterized by lower expression of CD24 and E-cadherin in comparison to primary breast luminal cells not having undergone a treatment of steps a)-d).

In yet a further aspect, the present invention relates to a differentiated cell derived from a multipotent mammary stem cell or a culture thereof according to the present invention, wherein said differentiated cell is a luminal cell or a myoepithelial cell.

In yet a further aspect, the present invention relates to a tissue of differentiated cells or an organ of differentiated cells derived from multipotent mammary stem cells or a culture thereof according to the present invention.

In yet a further aspect, the present invention relates to a multipotent mammary stem cell or culture thereof according to the present invention for use in a method of tissue engineering, transplantation, tissue reconstruction, cell therapy procedures, in particular autologous cell therapy procedures, a method of treating the effects of mastectomy or a method of breast enlargement, reconstruction or engineering, wherein said use comprises the administration of such multipotent mammary stem cells or differentiated cells derived therefrom to a patient in need thereof.

In yet a further aspect, the present invention relates to a use of a multipotent stem cell according to the present invention for the manufacture of a medicament for a method of tissue engineering, transplantation, tissue reconstruction, cell therapy procedures, in particular autologous cell therapy procedures, a method of treatment of the effects of mastectomy or a method of breast enlargement, reconstruction or engineering.

In yet a further aspect, the present invention relates to a method of tissue engineering, transplantation, tissue reconstruction, cell therapy procedure, treatment of the effects of mastectomy, comprising the steps:

generating multipotent mammary stem cells according to the present invention by a method in accordance with the present invention, and applying/administering such multipotent mammary stem cells to a patient in need thereof at a place of the patient's body where a process of tissue engineering, transplantation, tissue reconstruction or cell therapy procedure is desired.

In one embodiment, such method is a cosmetic method or is a medical treatment method.

FIGS. 1A-1B are photographs of an immunoblotting analysis and flow cytometry. Serum-free conditioned medium (SFCM) from active fibroblasts or the recombinant IL-8 protein (25 ng/ml) were added onto breast primary normal luminal cells (PNLC) for 24 hours. In one embodiment, the serum-free conditioned medium (SFCM) is a 1:1-mixture of M199 medium and F12 medium which is supplemented with ≤0.2% (vol/vol) serum, preferably fetal bovine serum (FBS), and 1% antibiotic-antimycotic solution (as described above). Serum-free medium (SFM) was used as negative control. In one embodiment, the serum-free medium used as negative control is a 1:1-mixture of DMEM and F12 medium or a 1:1 mixture (vol/vol) of M199 medium and F12 medium, either mixture being supplemented with ≤0.2% (vol/vol) serum, preferably fetal bovine serum, 1% antibiotic-antimycotic solution, HuMEC supplement solution (Gibco cat. 12754-016) (as described above) and bovine pituitary extract (5 µg/ml). All percentage values indicated herein and hereafter are vol./vol.-percentages, if not indicated otherwise.

The immunoblotting analysis in FIG. 1A shows a strong decrease in the epithelial marker E-cadherin, while the mesenchymal marker N-cadherin was up-regulated in cells that were exposed to IL-8 or active fibroblasts, indicating the induction of the EMT ("epithelial mesenchymal transition") process in these cells. FIG. 1A shows a clear decrease in CD24, while CD44 and ALDH1/2 were up-regulated as compared to their levels in control cells. Similarly, the two stemness transcription factors OCT4 and KLF4 were also strongly increased in PNLC cells exposed to SFCM from active fibroblasts or IL-8 as compared to control cells exposed to SFM only (FIG. 1A). FIG. 1B includes graphs of the three test groups (SFM, IL-8 and serum-free conditioned medium from active fibroblasts, SFCM), which shows increase in the CD24$^{low}$/CD44$^{high}$ population in the PNLC cells exposed to SFCM from active fibroblasts or IL-8 as compared to control cells exposed to SFM only (FIG. 1B).

Figure 2A:
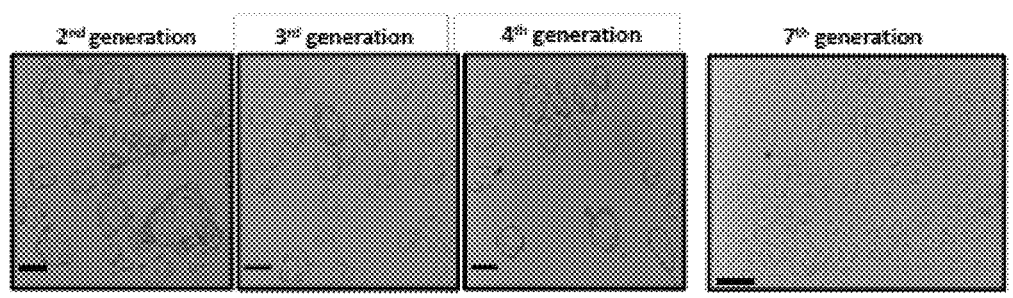
FIGS. 2A-2B are graphs showing the SFCM-dependent formation of typical hollow mammospheres (50-200 μm) with self-renewal capacity that is lost over time with generations. After >7 generations mammosphere formation is virtually lost.
Figure 2B:
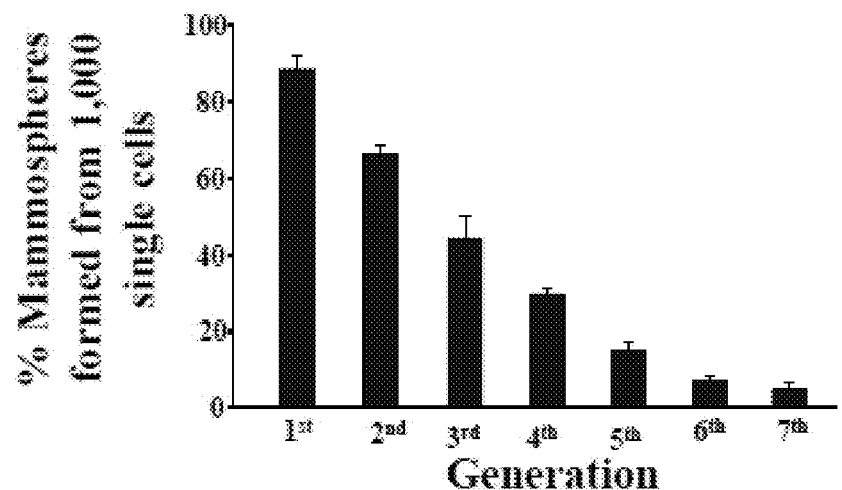

FIGS. 2A-2B are graphs showing the SFCM-dependent formation of typical hollow mammospheres (50-200 µm) with self-renewal capacity that is lost over time with generations. After >7 generations mammosphere formation is virtually lost.

Figure 3A:
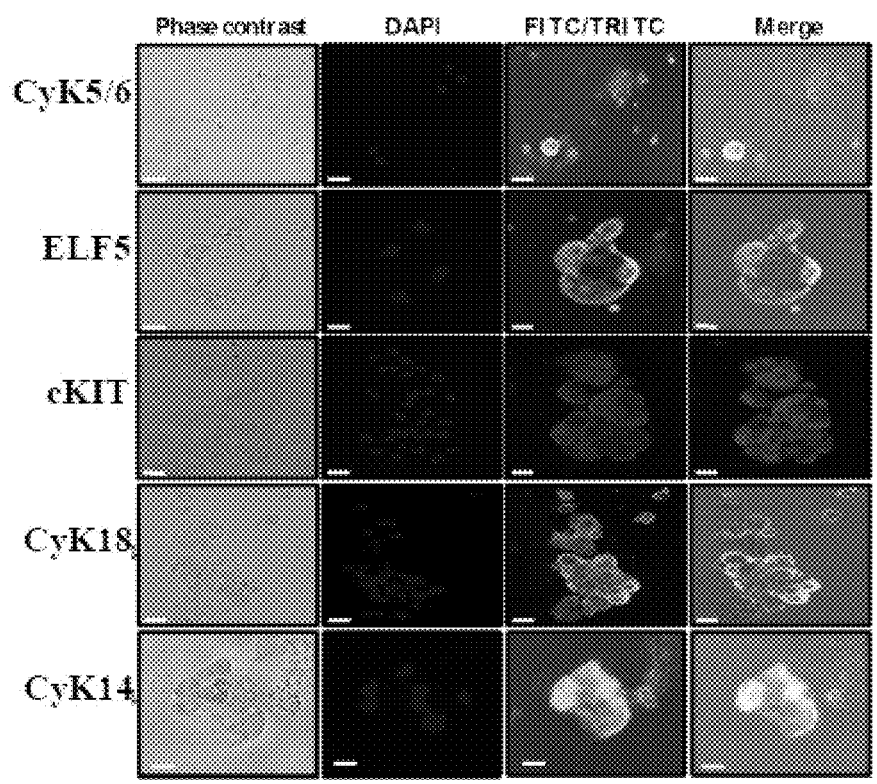

FIGS. 3A-3B are graphs of immunofluorescence test on the mammospheres obtained by the treatment with SFCM from active fibroblasts (A) OR IL-8. FIG. 3A shows that the spheres were positive for the mammosphere-specific markers cytokeratines (CyK) 5/6, 18 and 14 as well as c-Kit and Elf-5. DAPI, FITC and TRITC were used as dyes (DAPI=4', 6-Diamidino-2-phenylindole; FITC=fluorescein isothiocyanate, TRITC=tetramethyl rhodamine). Similarly, FIG. 3B presents the results obtained for cells treated with IL-8 for the mammosphere-specific markers cytokeratines 14, and 19. as well as Merge, DAPI and Merge/DAPI. "Merge" is the overlay between the 2 antibodies, and "Merge/DAPI" is the overlay between Merge and DAPI.

The staining of CyK5, 6, 14, 18 and 19 and/or of ELF-5 and c-Kit indicates a dedifferentiation and the presence of stem cell features/progenitor features. In particular, the double staining for CyK14 and 19 is indicative of such progenitor features.

FIG. 4A-4B are graphs showing that the multipotent stem cells obtained by the method of the present invention exhibit high and exponential proliferative capacity as well as a high telomerase activity which is also an indicator of stemness. FIG. 4A shows the proliferation rate, and FIG. 4B shows the telomerase activity. 293FT cells are embryonic stem cells having a high telomerase activity and serving as a positive control; cells treated with merely serum-free medium ("SFM") do not have a pronounced telomerase activity and serve as a negative control; primary breast luminal cells treated with conditioned medium from active fibroblasts ("AF") in accordance with the present invention also have a high telomerase activity. The heat treatment mentioned in the figure ("+ Heat", "− Heat") refers to the exposure to heat at 85 C for 10 min. Such heat treatment serves to destroy telomerase activity and is used as negative control.

Figure 5B:
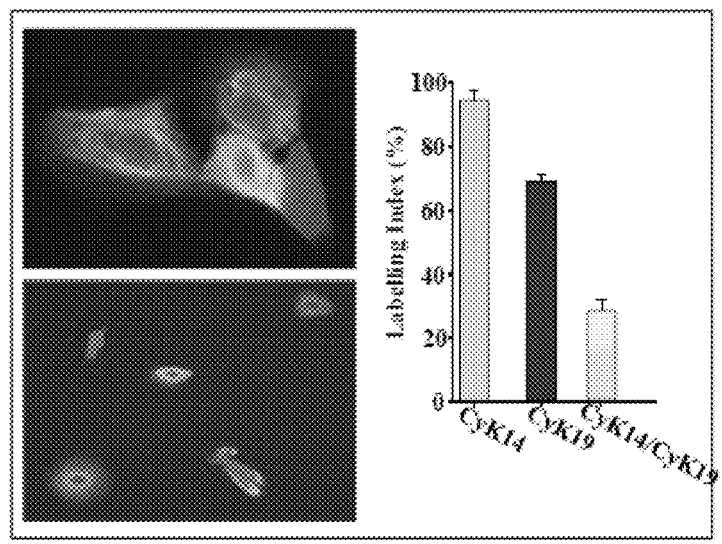
Figure 5C:
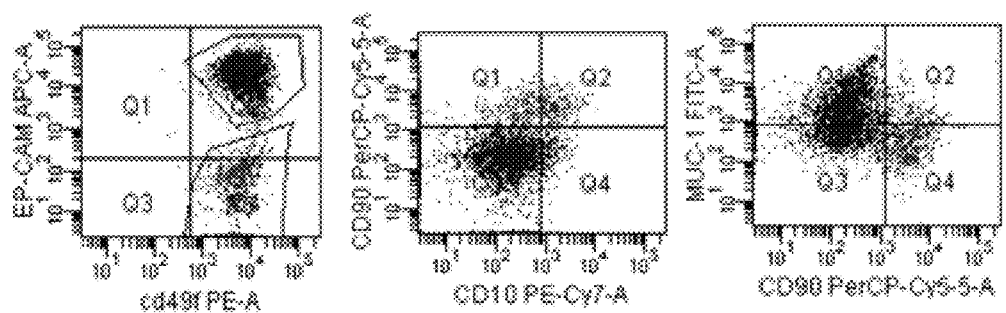

FIG. 5A-5C illustrates the differentiation capacity of the SFCM generated multipotent stem cells obtained by the method of the present invention. FIG. 5A shows the presence of cells with luminal and myoepithelial morphology. FIG. 5B illustrates a stain test for luminal and myoepithelial morphology for the cells produced according the method of the present invention. As shown by FIG. 5B, these cells were stained positive for the myoepithelial marker (CyK14), or the luminal marker (CyK19) or both, with lower proportion of cells that were positive for both. This indicates the ability of these mammary stem cells in the mammospheres to be differentiated into luminal and myoepithelial cells, in addition to some bipotent cells. FIG. 5C is a graph of a flow cytometry analysis showing two different populations, one corresponding to myoepithelial cells and the other one corresponding to a luminal type of cells.

FIG. 6 illustrates the differentiation capacity of the IL-8-generated mammospheres. Similar to the results shown in FIG. 5, FIG. 6 shows that these mammospheres were positive for both cytokeratin-14 and cytokeratin-19.

FIG. 7 shows that both IL-8- and SFCM-induced mammospheres were able to differentiate into branches on gelatin in the presence of matrigel and prolactin, which are typical structures of the branching ducts that compose the mammary gland.

The present invention successfully provides methods by which serum-free conditioned medium from active breast fibroblasts ("SFCM") or IL-8 are used to dedifferentiate breast primary normal luminal cells into multipotent mammary stem cells.

As used herein, a "stem cell" is a multipotent cell, which possesses two properties: 1. The ability of self-renewal; 2. The capacity to differentiate into more than one type of specialized cell types.

The term "self-renewal" refers to the ability to go through numerous cycles of cell division while maintaining an undifferentiated state. Self-renewal implies the proliferation and the maintenance of an undifferentiated state.

As used herein, a "proliferative capacity" refers to a stem cell that is rapidly dividing, for example, at a rate of one division every 24, 48, 72, 96, or 120 hours. In one embodiment, such proliferative capacity is an exponential proliferative capacity.

As used herein, the term "conditioned medium" is medium in which cells have been cultured for a period of time as opposed to media fresh out of the bottle.

As used herein, "stemness" represents the properties of stem cells. All the experiments were performed to show the stemness of the obtained cells as measured e.g. by cytokeratines, self renewal, telomerase activity and differentiation. Hence, "stemness" is exemplified by the expression or overexpression of cytokeratines, in particular cytokeratines 5, 6, 14, 18 and/or 19, the capability of self renewal, a high telomerase activity and the capability of differentiation.

As used herein, the term "patient" represents a human being, or a non-human animal, e.g. a non-human mammal, like a dog, a cat, a rat, a monkey or livestock animals, such as cow, pig, sheep or horse.

As used herein, the term "epithelial-mesenchymal transition (EMT)" refers to a process by which the epithelial cells lose their cell polarity, cell adhesion and gain migratory and invasive properties to become mesenchymal cells. EMT is a transition phase toward stemness.

As used herein, E-cadherin is a known member of the cadherin family. In adult tissues, E-cadherin is expressed in epithelial tissues. In stem cells, the level of E-cadherin is reduced in comparison to differentiated cells.

As used herein, N-cadherin is a protein that in humans is encoded by the CDH2 gene. N-cadherin is a transmembrane protein expressed in multiple tissues and functions to mediate cell-cell adhesion. In stem cells, the level of N-cadherin is increased in comparison to differentiated cells.

As used herein, the term "differentiation" refers to the process where a cell changes from one cell type to another. A cell that can differentiate into all cell types of the adult organism is known as pluripotent. Pluripotent stem cells undergo further specialization into multipotent progenitor cells that then give rise to functional cells.

As used herein, the term "multipotent" with respect to stem cells of the invention, refers to the limited ability of the stem cells to give rise to a number of specialized cells. A multipotent stem cell is limited in its ability to differentiate in only a number of types of cells, but not in all types of cells. Examples of multipotent stem cells include those in the brain that give rise to different neural cells and glia, or haematopoietic cells, which can give rise to different blood cell types, but they cannot create brain cells. Multipotent mammary stem cells can give rise to and differentiate into luminal cells and myoepithelial cells as well as bipotent stem cells.

Mammary stem cells are multipotent adult stem cells that typically reside in the mammary gland as their normal site of residence, can self-renew by dividing and can differentiate into all specialized mammary epithelial cells, i.e. luminal cells and myoepithelial cells.

As used herein, Interleukins are a group of cytokines (secreted proteins and signal molecules) that were first seen to be expressed by white blood cells (leukocytes). Interleukin-8 is an interleukin responsible for the recruitment of leukocytes and a promoter of angiogenesis. Human IL-8 has the amino acid sequence represented by MTSKLAVAL-LAAFLI SAALCEGAVLPRSAKELRCQCIKTYSKPFHP-KFIKELRVIESGPHCA NTEIIVKLSDGRELCLDPKEN-WVQRVVEKFLKRAENS (SEQ ID NO:1).

As used herein, the term "isolated" refers to an epithelial cell, a stem cell or population of daughter stem cells in a non-naturally occurring state outside of the body (e.g. isolated from the body or a biological sample from the body).

As used herein, the term "lineage" refers to a pathway of cellular development, in which precursor or "progenitor" cells undergo progressive physiological changes to become a specified cell type having a characteristic function. For example, the human multipotent mammary stem cell can differentiate into the lineage of myoepithelial cell and the luminal cell.

As used herein, the term "population" is meant to refer to a collection of at least ten cells. Preferably, the population consists of at least twenty cells, more preferably at least one hundred cells, and most preferably at least one thousand, or even one million cells.

As used herein, the term "autologous," as used herein, refers to cells derived from the same subject. In contrast, "heterologous" refers to cells derived from a different subject.

Throughout this application, various media are mentioned and described as being used. For example, the media M199, F12 and DMEM are repeatedly mentioned as being components of the media used in the method according to the present invention. M199 is a tissue culture medium well known (see original publication by Morgan et al., Proc. Soc. Exp. Biol. Med. 73, 1 (1950)), and includes Earle's salts, L-glutamine and sodium bicarbonate. It is commercially available from various manufacturers, such as Sigma Aldrich, Thermo Fischer and others. F12 medium is another medium that is well known and used in cell culture and is also commercially available from various manufacturers, including Sigma Aldrich, Gibco, Thermo Fischer, Lonza and others. DMEM is Dulbecco's modified Eagle's medium and is also available from a number of manufacturers, including Sigma Aldrich and others. B27 is a medium supplement that is well known and that is commercially available from various manufacturers.

"Active breast stromal fibroblasts" as used herein, are breast fibroblasts that express high level of α-SMA, SDF-1 and other cytokines, such as IL-6 and IL-8. Typically, they have a flat and large morphology and show higher proliferative, migratory and invasive abilities in comparison to non-active breast stromal fibroblasts. These cells can be obtained from breast cancer tissues as cancer associated fibroblasts (CAFs) or e.g. by treating primary breast stromal fibroblasts with IL-6, as e.g. shown in Hendrayani et al. JBC 2014: 289: 30962-60976.

The invention is now further described by reference to the following examples which are given to illustrate not to limit the present invention.

Examples

Materials and Methods

Serum-free conditioned medium (SFCM) (as described above) from active fibroblasts (AF) or recombinant IL-8 protein (25-100 ng/ml) were added onto breast primary normal luminal cells (PNLC) for 24 hours. Serum-free medium (SFM) (as described above) was used as negative control.

Isolation of Primary Breast Luminal Cells

Breast tissues collected from reduction mammoplasty were immediately minced and digested with collagenase (0.25% collagenase, 5 mM glucose and 1.5% BSA in PBS) and agitated with Adams Nutator Mixer at 37° C. overnight. Cell suspension was centrifuged at 800×g for 8 minutes at 4° C. Fat were aspirated and cell pellets were re-suspended in PBS. Cells were differentially centrifuged at 120×g for 2 minutes at 4° C. to enrich for epithelial cells. The epithelial-enriched pellet was further digested with accutase (Stem Cell Technologies) at 37° C. for 60 minutes until organoids disaggregated into single cells. Epithelial cells were washed once with PBS, filtered through a 70 µm mesh (BD Falcon, Bedford), and then were re-suspended in growth medium (DMEM/F12 1:1, 2% Fetal Bovine Serum, 1% Antibiotic-Antimycotic, HMEC Supplementary kit and bovine pituitary extract (5 µg/ml) (Gibco).

The identity of the primary cells was confirmed prior to use by immunofluorescence (Cytokeratin 18+, cytokeratin 19$^+$ Cytokeratin 14$^-$) and flow cytometry (EpCam$^+$/CD49f$^-$).

Results

An immunoblotting analysis in FIG. 1A shows a strong decrease in the epithelial marker E-cadherin, while the mesenchymal marker N-cadherin was up-regulated in cells that were exposed to IL-8 or serum-free conditioned medium from active fibroblasts (AF-SFCM), indicating the induction of the EMT (epithelial to mesenchymal transition) process in these cells. Since EMT is a transition phase toward stemness, the inventors investigated this possibility in response to SFCM from AF and IL-8. FIG. 1A shows clear decrease in CD24, while CD44 and ALDH1/2 were up-regulated as compared to their levels in control cells. Similarly, the levels of the two stemness transcription factors OCT4 and KLF4, OCT4, octamer-binding transcription factor 4, and KLF4, Kruppel-like factor 4 were also strongly increased in PNLC cells exposed to AF-SFCM or IL-8 as compared to control cells. These results were confirmed by flow cytometry (CD24/CD44) (FIG. 1B). This suggests the possible induction of stemness in breast luminal cells when exposed to SFCM from active breast stromal fibroblasts or recombinant IL-8.

Experiment on the Formation of Mammospheres (Steps a, b, c and d)

To confirm the stemness of the AF- and IL-8-treated luminal cells, cells were first cultured in suspension in the presence of stem cells specific culture medium till the formation of mammospheres.

FIG. 2A, B shows the AF-SFCM-dependent formation of typical hollow mammospheres with self-renewal capacity that has been lost over time with generations.

Experiment on Mammosphere-Specific Markers

The presence of some mammosphere-specific markers (cytokeratines 5/6, 18 and 14, c-Kit and Elf-5) were tested by immunofluorescence, and it could be shown that the spheres were positive for the cytokeratines 5/6, 18 and 14 as well as c-Kit and Elf-5 (FIG. 3A). Similar results were obtained for cells treated with IL-8 (FIG. 3B).

This indicates the presence of various progenitor features (e.g. double staining for CyK14/19) in these cells.

Immunofluorescence

Cells were fixed with 4% paraformaldehyde for 10 min, permeabilized with 0.2% Triton X-100 for 10 min and quenched in 100 mM glycin for 10 min at room temperature. Cells were then blocked in 10% FCS and incubated with primary antibody. Cells were then washed and incubated with the Alexa Fluor-594 or -488 conjugated antibodies, respectively (Life technologies). Nuclei were stained with DAPI (Vectror laboratories, Inc) and Images were captured using Floid Cell Imaging Station (Life technologies). Primary antibodies used: Cytokeratin 14 (LL002), Cytokeratin 19 (EP1580Y), Cytokeratin 18, Cytokeratin 5/6, c-Kit and ELF5 were purchased from Abcam.

Proliferative Test

For mammospheres proliferation, mammospheres were digested into single cells and sieved through a 40 µm sieve, and then were analyzed microscopically for single-cellularity. 1000 single cells were plated in ultralow attachment 96-well plate (corning) in stem cell specific medium and counted weekly upon separation by digestion.

Interestingly, these cells also exhibited high and exponential proliferative capacity as well as high telomerase activity (FIG. 4A, 4B).

Telomerase Activity Assay

Telomerase activity assay was performed using TeloTAGGG Telomerase PCR ELISA assay (Roche) as instructed by the manufacturer. Briefly, 20 µg of heat- or sham-treated cell extracts were amplified by PCR (94° C. for 30 sec, 50° C. for 30 sec and 72° C. for 90 sec). The PCR products were hybridized to anti-digoxigenin-peroxidase and then ELISA reaction was performed and the OD was measured at 450 nm on a standard ELISA plate-reader (x-Mark, BIO-RAD). The heat treatment mentioned above and in FIG. 4 ("+ Heat", "− Heat") refers to the exposure to heat at 85 C for 10 min. Such heat treatment serves to destroy telomerase activity and is used as negative control.

Differentiation Capacity Test

Mammospheres were dissociated into single cells and seeded onto 0.1% gelatin coated plates at at a density of 2000 viable cells/10 cm-diameter dishes. Cells were grown in luminal medium and after 48 hrs cell Images were captured using Floid Cell Imaging Station (Life technologies). Differentiated cells were utilized to assess the luminal and myoepithelial markers by immunofluorescence.

To further confirm the progenitor nature of these cells, the inventors assessed their differentiation capacity. Therefore, freshly obtained mammospheres were plated on gelatin for 1 week, and then they were characterized by flow cytometry and immunostaining.

Flow Cytometry

Cells were fixed by 0.5% paraformaldehyde in PBS for 15 min, permeabilized (permeabilization buffer, eBioscience), and incubated for 30 min on ice with directly labeled antibodies. Cells were then washed and re-suspended in 300 µL PBS. Data were acquired using LSR II flow cytometer using FACSDIVA software (BD). Positive staining was considered based on the negativity of an isotype control. A minimum of 10,000 events were recorded for all samples.

FIG. 5A shows the presence of cells with luminal and myoepithelial morphology. These cells were stained positive for the myoepithelial marker (CK14), or the luminal marker (CK19) or both, with lower proportion of cells that were positive for both (FIG. 5B). This indicates the ability of these mammospheres to be differentiated into luminal and myoepithelial cells, in addition to some bipotent/undifferentiated cells. Moreover, flow cytometry analysis showed 2 different populations one corresponding to myoepithelial cells and the other one corresponds to luminal type of cells (FIG. 5C).

Similar results were obtained from IL-8-generated mammospheres (FIG. 6). These mammospheres were positive for both cytokeratin-14 and cytokeratin-19 (FIG. 6).

Branching Ability Test

Finally, the present inventors sought to investigate the branching ability. Branching is a form of differentiation into branch structures like those that are present in the mammary gland. In vitro the process is induced in gelatin in the presence of matrigel and prolactin of the formed mammospheres on gelatin in the presence of matrigel and prolactin. FIG. 7 shows that both IL-8- and SFCM-induced mammospheres were able to differentiate into branches, which are typical structures of the branching ducts that compose the mammary gland.

Differentiation

Mammospheres were dissociated into single cells and seeded onto 0.1% gelatin coated plates at at a density of 2000 viable cells/10 cm-diameter dishes. Cells were grown in luminal medium and after 48 hrs cell Images were captured using Floid Cell Imaging Station (Life technologies). Differentiated cells were utilized to assess the luminal and myoepithelial markers by immunofluorescence.

Branching

To test the alveolar differentiation, cells were differentiated, as described above, and after 5 days, a layer of Matrigel (BD Biosciences) was added as well as prolactin (1 µg/ml). The complex acinar and branched-acinar structures formed after 3 days of plating were imaged using Floid Cell Imaging Station (Life technologies).

Conclusion

Together, these results indicate that serum-free conditioned medium from breast active fibroblasts or IL-8 are capable of dedifferentiating breast normal luminal cells into multipotent mammary stem cells.

The invention is now further described by reference to the following embodiments, which are given to illustrate, not to limit the invention:

1. A method for generating multipotent mammary stem cells comprising the steps:
   a) isolating and growing primary breast luminal cells in-vitro;
   b) treating the primary breast luminal cells with either a conditioned medium from active breast stromal fibroblasts or with interleukin-8 (IL-8) in serum-free medium;
   c) continuing the growth of cells until the formation of cellular aggregates, wherein preferably such growth is done in a breast luminal-cell-specific medium; and
   d) transferring the cells to a stem cell growth medium and growing them further until the formation of mammospheres.

2. The method according to embodiment 1, wherein the conditioned medium from active breast stromal fibroblasts of step b) comprises a 1:1 mixture (vol/vol) of M199 medium and F12 medium, supplemented with 0%-1% (vol/vol) serum, preferably ≤0.2% (vol/vol) serum, preferably fetal bovine serum (FBS), preferably 0.2% (vol/vol) FBS, and 0.1%-2% (vol/vol) of an antibiotic-antimycotic solution, said antibiotic-antimycotic solution comprising 10,000 units/ml penicillin, 10000 µg/ml streptomycin and 25 µg/ml amphotericin B, preferably 1% of said antibiotic-antimycotic solution, and wherein the serum-free medium of step b)
   comprises a 1:1 mixture (vol/vol) of M199 medium and F12 medium, said mixture being supplemented with 0%-1% (vol/vol) serum, preferably ≤0.2% (vol/vol) serum, preferably fetal bovine serum (FBS), preferably 0.2% (vol/vol) FBS, 0.1%-2% of an antibiotic/-antimycotic solution, said antibiotic-antimycotic solution comprising 10,000 units/mil penicillin, 10000 µg/ml streptomycin and 25 µg/ml amphotericin B, preferably 1% (vol/vol) of said antibiotic-antimycotic solution.

3. The method according to any of embodiments 1-2, wherein, in step c) growth of the cells is performed in a breast luminal cell-specific medium, wherein said breast luminal cell-specific medium comprises a 1:1 mixture (vol/vol) of DMEM medium and F12 medium supplemented with 1%-20% (vol/vol) serum, preferably fetal bovine serum (FBS), preferably 2% (vol/vol), 0.1%-2% (vol/vol) of an antibiotic-antimycotic solution, said antibiotic-antimycotic solution comprising 10,000 units/ml penicillin, 10000 µg/ml streptomycin and 25 µg/ml amphotericin B, preferably 1% (vol/vol) of said antibiotic-antimycotic solution, and bovine pituitary extract (5 µg/ml).

4. The method according to any of embodiments 1-3, wherein said stem cell growth medium in step d) comprises MEBM medium, supplemented with 0.1%-2% (vol/vol) of an antibiotic-antimycotic solution, said antibiotic-antimycotic solution comprising 10,000 units/ml penicillin, 10000 µg/ml streptomycin and 25 µg/ml amphotericin B, preferably 1% (vol/vol) of said antibiotic-antimycotic solution, B27®-supplement at 0.1%-10% (vol/vol), preferably 2% (vol/vol), epidermal growth factor (EGF) at 20 ng/ml, Hydrocortisone at 500 ng/ml, and recombinant human insulin-like growth factor-1 at 1-10 µg/ml, preferably 5 µg/ml.

5. The method according to any of the foregoing embodiments, wherein treating in step b) is done for a period in the range of from 12 hours to 120 hours, preferably in the range of from 12 hours to 72 hours, more preferably in the range of from 12 hours to 48 hours, even more preferably in the range of from 12 hours to 36 hours, even more preferably in the range of from 12 hours to 30 hours, even more preferably in the range of from 20 hours to 28 hours.

6. The method according to any of the foregoing embodiments, wherein the primary breast luminal cells are primary human breast luminal cells, and the multipotent mammary stem cells are multipotent human mammary stem cells.

7. The method according to any of the foregoing embodiments, wherein said interleukin-8 is recombinant interleukin-8.

8. The method according to any of the foregoing embodiments, wherein said interleukin-8 is human interleukin-8, preferably having an amino acid sequence represented by
   MTSKLAVALLAAFLISAALCEGAVLPRSAKELRC-QCIKTYSKPFHPKFIKELRVIES GPHCANTEIIVKLS-DGRELCLDPKENWVQRVVEKFLKRAENS (SEQ ID NO:1).

9. The method according to any of the foregoing embodiments, wherein said interleukin-8 is used in step b) at a concentration in the range of from 25 ng/mL to 100 ng/mL, preferably 100 ng/mL.

10. The method according to any of the foregoing embodiments, wherein said primary breast luminal cells are identified and isolated based on their expressing at least one or a combination of the following markers selected from Cytokeratin 18, Cytokeratin 19 and epithelial cell adhesion molecule (EpCam), wherein they are selected and isolated if they express such marker(s), and are not selected and isolated if they do not, and/or wherein said primary breast luminal cells are identified and isolated based on their not expressing at least one or a combination of the following markers selected from Cytokeratin 14 and integrin α-6 (CD49f), wherein they are selected and isolated if they do not express such marker(s), and are not selected and not isolated if they do, and wherein preferably, isolation occurs by enzymatic digestion using one or several proteolytic and/or collagenolytic enzyme(s) and subsequent centrifugation.

11. The method according to any of embodiments 1-10, wherein the growing of said cells in step d) occurs in an environment that favors suspension cell culture, e.g. plates or dishes with a low attachment substrate.

12. The method according to any of embodiments 1-11, wherein the formed mammospheres have a size in the range of from 50 µm to 200 µm.

13. The method according to any of the foregoing embodiments, wherein the multipotent mammary stem cells are produced by the performance of steps a)-d) and are characterized by an up-regulation of one or several or all of CD44, ALDH1, ALDH2, OCT4, KLF4 and N-cadherin, and the simultaneous expression of one or several or all myoepithelial and luminal markers selected from CyK5, CyK6, CyK14, CyK18, CyK9, c-Kit, Elf-5, in comparison to cells of the same type, i.e. primary breast luminal cells, not having undergone a treatment of steps a)-d), and are further characterized by a lower expression of CD24 and E-cadherin in comparison to primary breast luminal cells not having undergone a treatment of steps a)-d).

14. The method according to any of the foregoing embodiments, further comprising the step of isolating said mammary stem cells.

15. A multipotent mammary stem cell or a culture of multipotent mammary stem cells generated by the method according to any of embodiments 1-14, said stem cell(s) being capable of differentiating into luminal cells and myoepithelial cells and being characterized by an up-regulation of one or several or all of CD44, ALDH1, ALDH2, OCT4, KLF4 and N-cadherin, and the simultaneous expression of one or several or all myoepithelial and luminal markers selected from CyK5, CyK6, CyK14, CyK18, CyK19, c-Kit, Elf-5, in comparison to cells of the same type, i.e. primary breast luminal cells, not having undergone a treatment of steps a)-d), and are further characterized by an lower expression of CD24 and E-cadherin in comparison to primary breast luminal cells not having undergone a treatment of steps a)-d).

16. A differentiated cell derived from a multipotent mammary stem cell or a culture thereof according to embodiment 15, wherein said differentiated cell is a luminal cell or a myoepithelial cell.

17. A tissue of differentiated cells or an organ of differentiated cells derived from multipotent mammary stem cells or a culture thereof according to embodiment 15.

18. The multipotent mammary stem cell or culture thereof according to embodiment 15 for use in a method of tissue engineering, transplantation, tissue reconstruction, cell therapy procedures, in particular autologous cell therapy procedures, a method of treating the effects of mastectomy or a method of breast enlargement, reconstruction or engineering, wherein said use comprises the administration of such multipotent mammary stem cells or differentiated cells derived thereof from to a patient in need thereof.

19. Use of a multipotent stem cell according to embodiment 15 for the manufacture of a medicament for a method of tissue engineering, transplantation, tissue reconstruction, cell therapy procedures, in particular autologous cell therapy procedures, a method of treatment of the effects of mastectomy or a method of breast enlargement, reconstruction or engineering.

20. A method of tissue engineering, transplantation, tissue reconstruction, cell therapy procedure, treatment of the effects of mastectomy, comprising the steps:
   generating multipotent mammary stem cells according to embodiment 15 by a method in accordance with any of embodiments 1-14, and
   applying/administering such multipotent mammary stem cells to a patient in need thereof at a place of the patient's body where a process of tissue engineering, transplantation, tissue reconstruction or cell therapy procedure is desired.

21. The method according to embodiment 20, which is a cosmetic method or which is a medical treatment method.

The features of the present invention disclosed in the specification, the claims and/or in the accompanying drawings may, both separately and in any combination thereof be material for realizing the invention in various forms thereof. Further modifications of the preferred embodiments are possible without leaving the scope of the invention which is solely defined by the claims.

REFERENCES

1. Deng et al., Loss of heterozygosity in normal tissue adjacent to breast carcinomas. Science 1996, 274:2057-2059;
2. Lakhani et al., Detection of allelic imbalance indicates that a proportion of mammary hyperplasia of usual type are clonal, neoplastic proliferations. Lab Invest 1996, 74:129-135.
3. Ercan, et al., Mammary Development and Breast Cancer: The Role of Stem Cells, Curr Mol Med. 2011 June; 11(4): 270-285
4. Internet, World Cancer Research Fund International, http://www.wcrf.org/int/cancer-facts-figures, accessed on Jun. 9, 2016
5. Kordon E C, Smith G H, an entire functional mammary gland may comprise the progeny from a single cell. Development. 1998; 125:1921-30
6. Wang R H, the new portrait of mammary gland stem cells. Int J Biol Sci 2006; 2(4):186-187
7. Shackleton M., et al., Nature. 2006 Jan. 5; 439(7072):84-8

We claim:

1. A method for generating multipotent mammary stem cells comprising the steps:
   a) isolating and growing primary breast luminal cells in-vitro;
   b) treating the primary breast luminal cells with either a conditioned medium from active breast stromal fibroblasts or with interleukin-8 (IL-8) in serum-free medium;
   c) continuing the growth of cells until the formation of cellular aggregates; and
   d) transferring the cells to a stem cell growth medium and growing them further until the formation of mammospheres.

2. The method according to claim 1, wherein the conditioned medium from active breast stromal fibroblasts of step b) comprises a 1:1 mixture (vol/vol) of M199 medium and F12 medium, supplemented with 0%-1% (vol/vol) serum, and 0.1%-2% (vol/vol) of an antibiotic-antimycotic solution, said antibiotic-antimycotic solution comprising 10,000 units/ml penicillin, 10000 μg/ml streptomycin and 25 μg/ml amphotericin B.

3. The method according to claim 1, wherein, in step c) growth of the cells is performed in a breast luminal cell-specific medium, wherein said breast luminal cell-specific medium comprises a 1:1 mixture (vol/vol) of DMEM medium and F12 medium supplemented with 1%-20% (vol/vol) serum, and supplemented with 0.1%-2% (vol/vol) of an antibiotic-antimycotic solution, said antibiotic-antimycotic solution comprising 10,000 units/ml penicillin, 10000 μg/ml streptomycin and 25 μg/ml amphotericin B.

4. The method according to claim 1, wherein said stem cell growth medium in step d) comprises MEBM medium, supplemented with 0.1%-2% (vol/vol) of an antibiotic-antimycotic solution, said antibiotic-antimycotic solution comprising 10,000 units/ml penicillin, 10000 μg/ml streptomycin and 25 μg/ml amphotericin B.

5. The method according to claim 1, wherein treating in step b) is done for a period in the range of from 12 hours to 36 hours.

6. The method according to claim 1, wherein the primary breast luminal cells are primary human breast luminal cells, and the multipotent mammary stem cells are multipotent human mammary stem cells.

7. The method according to claim 1, wherein said interleukin-8 is recombinant interleukin-8.

8. The method according to claim 1, wherein said interleukin-8 is human interleukin-8 having an amino acid sequence represented by
MTSKLAVALLAAFLISAALCEGAVLPRSAKELRC-QCIKTYSKPFHPKFIKELRVIESGPHCANTEIIV KLSDGRELCLDPKENWVQRVVEKFLKRAENS (SEQ ID NO:1).

9. The method according to claim 1, wherein said interleukin-8 is used in step b) at a concentration in the range of from 25 ng/mL to 100 ng/mL.

10. The method according to claim 1, wherein said primary breast luminal cells are identified and isolated based on their expressing at least one or a combination of markers selected from Cytokeratin 18, Cytokeratin 19 and epithelial cell adhesion molecule (EpCam), wherein they are selected and isolated if they express such marker(s), and are not selected and isolated if they do not, and/or wherein said primary breast luminal cells are identified and isolated based on their not expressing at least one or a combination of the following markers selected from Cytokeratin 14 and integrin α-6 (CD49f), wherein they are selected and isolated if they do not express such marker(s), and are not selected and not isolated if they do.

11. The method according to claim 1, wherein the growing of said cells in step d) occurs in plates or dishes with a low attachment substrate.

12. The method according to claim 1, wherein the formed mammospheres have a size in the range of from 50 μm to 200 μm.

13. The method according to claim 1, wherein the multipotent mammary stem cells are produced by the performance of steps a)-d) and are characterized by an up-regulation of one or several or all of CD44, ALDH1, ALDH2, OCT4, KLF4 and N-cadherin, and the simultaneous expression of one or several or all myoepithelial and luminal markers selected from CyK5, CyK6, CyK14, CyK18, CyK19, c-Kit, Elf-5, in comparison to primary breast luminal cells not having undergone a treatment of steps a)-d), and are further characterized by a lower expression of CD24 and E-cadherin in comparison to primary breast luminal cells not having undergone a treatment of steps a)-d).

14. The method according to claim 1, further comprising the step of isolating said mammary stem cells.

* * * * *

UNITED STATES PATENT AND TRADEMARK OFFICE
CERTIFICATE OF CORRECTION

PATENT NO.       : 10,100,275 B2
APPLICATION NO.  : 15/461043
DATED            : October 16, 2018
INVENTOR(S)      : Abdelilah Aboussekhra et al.

It is certified that error appears in the above-identified patent and that said Letters Patent is hereby corrected as shown below:

In the Specification

Column 13,
Line 43, "50.2 % (vol/vol)" should read -- $\leq 0.2$ % (vol/vol) --.
Line 56, "10,000 units/mil" should read -- 10,000 units/ml --.

Column 15,
Line 6, "CyK9" should read -- CyK19 --.

Signed and Sealed this
Eighteenth Day of June, 2019

Andrei Iancu
*Director of the United States Patent and Trademark Office*